United States Patent [19]
White et al.

[11] Patent Number: 5,003,985
[45] Date of Patent: Apr. 2, 1991

[54] END TIDAL RESPIRATORY MONITOR

[75] Inventors: Curtis D. White; Billy L. Carpenter, both of San Antonio, Tex.

[73] Assignee: Nippon Colin Co., Ltd., Japan

[21] Appl. No.: 423,643

[22] Filed: Oct. 19, 1989

Related U.S. Application Data

[63] Continuation of Ser. No. 135,005, Dec. 18, 1987, abandoned.

[51] Int. Cl.$^5$ .............................................. A61B 5/08
[52] U.S. Cl. ................................... 128/716; 128/719; 128/725; 364/413.03
[58] Field of Search ............... 128/716, 719, 725, 671; 364/413.03, 413.05

[56] References Cited

U.S. PATENT DOCUMENTS

| | | | |
|---|---|---|---|
| 4,289,142 | 9/1981 | Kearns | 128/716 |
| 4,440,177 | 4/1984 | Anderson et al. | 128/719 |
| 4,463,764 | 8/1984 | Anderson et al. | 128/719 |

OTHER PUBLICATIONS

El-Dhaher et al., "Microprocessor-Based Data . . . Signals", Microprocess and Microsyst., vol. 5, No. 8, Oct. 1981, pp. 339-345.

Primary Examiner—Lee S. Cohen
Attorney, Agent, or Firm—Oliff & Berridge

[57] ABSTRACT

A method and apparatus for determining a number of important physiologic characteristics of a patient based on a end tidal determinations taken from a single respiratory waveform. In the preferred embodiment, breath detection, end-tidal occurrence, and respiratory information is determined using only the expired $CO_2$ gas concentration waveform. The system of the present invention is capable of performing the following basic functions: (1) identification of breath-by-breath inspired/expired end-tidal gas concentrations of three or more other expired gases (i.e., $O_2$, $NO_2$, and a volatile anesthetic); (2) calculation of the respiratory, inspiratory, and expiratory periods; (3) calculation of the respiratory rate and inspiratory/expiratory ratio; and (4) calculation of the multi-breath and time-trend averages.

The preferred embodiment of the invention system comprises a breath detection algorithm which is implemented in two phases—initialization and normal. The initialization phase tests for presence of a respiratory signal presence then determines the parameters necessary for the normal search phase. Initialization of the system requires no prior knowledge of the respiratory rate, end-tidal differences, or breathing type. The search method implemented in the normal search phase determines the occurrence of a breath by identifying the end-tidal inspired value for the next breath. Two independent search methods are used in the normal search phase. Each method identifies a potential candidate inspiration value. The candidate inspiration values are tested for appropriate amplitude. If the candidate inspiration value fails to satisfy predetermined values, the search process continues until a valid candidate is found or the detection search is reinitiated. In a situation where two candidate inspiration values are located, an arbitration procedure is implemented to determine whether one or both of the candidate inspired values is appropriate.

8 Claims, 15 Drawing Sheets

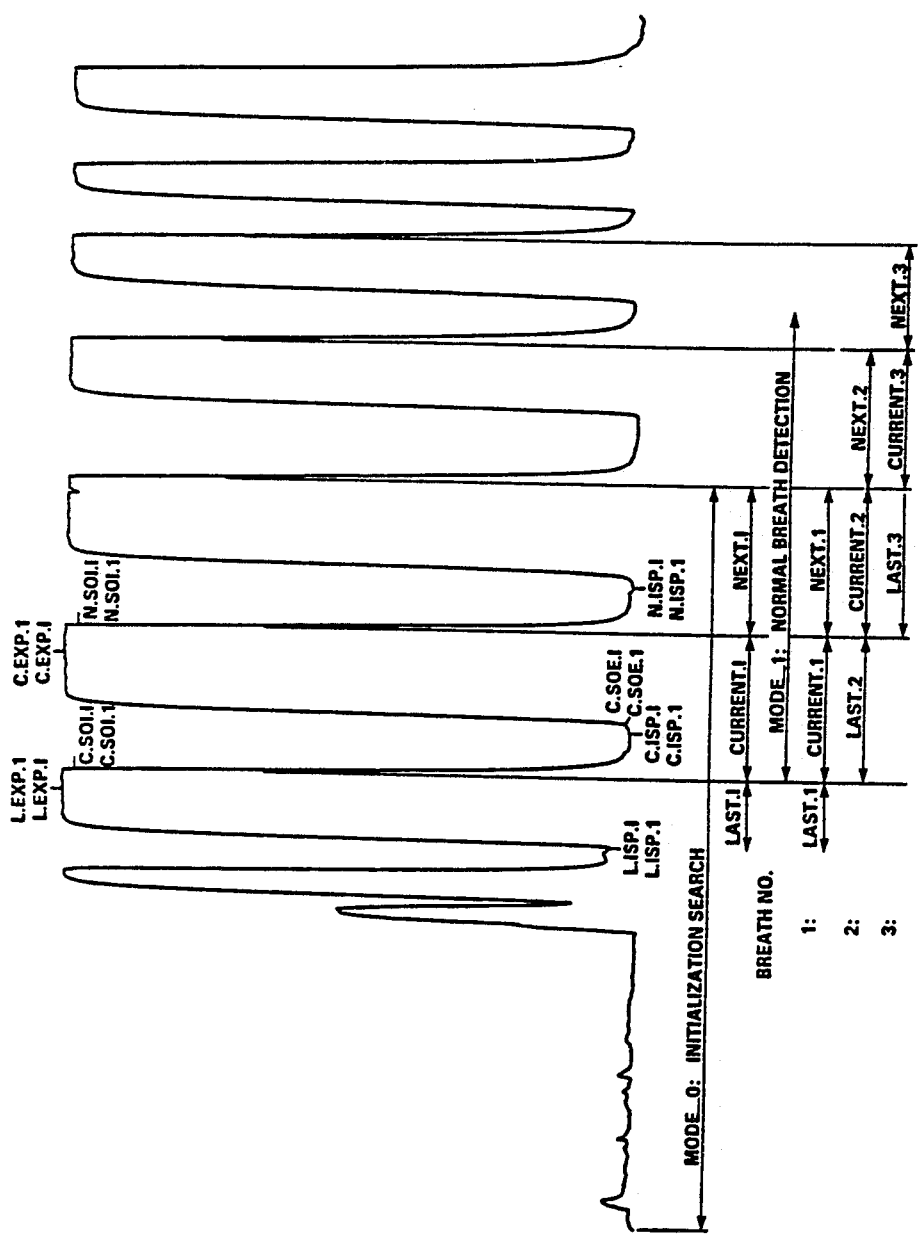

END TIDAL RESPIRATORY MONITOR

This is a continuation of co-pending U.S. patent application Ser. No. No. 07/135,005 filed on Dec. 18, 1987, now abandoned.

FIELD OF THE INVENTION

The present invention relates generally to the field of physiological monitoring systems. Specifically, the present invention provides a novel end tidal monitoring system which can be used to assist a physician in monitoring a patient's physiological condition and maintaining appropriate levels of anesthesia.

BACKGROUND

In recent years, the anesthesiologist's job has become increasingly complex with the addition of numerous independent monitoring systems and alarms which must be monitored in order to maintain the patient in the desired physiologic condition during an operation. It would be extremely desirable, therefore, to be able to provide the anesthesiologist with a single integrated system which can be used to monitor the patient. Such a system would contain an automatic, closed loop controller for the administration of a volatile gas anesthetic. In addition to the automatic control of the anesthetic, such a system should analyze the patients' physiologic and/or neurological condition in order to advise the anesthesiologist and to automatically maintain a preset anesthetic level or concentration.

The critical first step toward the development of the above-described system is an effective end-tidal respiratory monitor which is capable of determining and displaying the inspired/expired concentration of $CO_2$, $O_2$, and the volatile anesthetic gases. End-tidal gas concentrations provide relative estimates of gas concentrations in the blood and can be used as the feed-back signal for a closed anesthesia servo controller.

Numerous systems for controlling the delivery of anesthetic and monitoring of physiologic conditions have been disclosed in prior patents. For example, U.S. Pat. Nos. 3,799,149; 3,895,630; 4,233,842; 4,440,177; 4,233,842 and 4,368,740 describe various types of systems for monitoring physiologic parameters of a patient during the administration of an anesthetic. In addition, U.S. Pat. No. 3,910,261 discloses an end tidal gas analysis apparatus for analyzing concentrations of $CO_2$ in a patient's expired gases. Despite the advances shown in the above-mentioned references, however, the prior art has heretofore been lacking an effective method and apparatus for accurately determining the end tidal concentration of expired gases. In particular, there is a need for an effective monitoring system wherein a plurality of respiratory expired gas channels can be monitored based on the accurate determination of end tidal values for a single channel of expired gas, e.g., $CO_2$. The method and apparatus of the present invention, described in greater detail hereinbelow, fulfills this need.

SUMMARY OF THE INVENTION

The present invention provides an effective method and apparatus for determining a number of important physiologic characteristics of a patient based on a end tidal determinations taken from a single respiratory waveform. In the preferred embodiment, breath detection, end-tidal occurrence, and respiratory information is determined using only the expired $CO_2$ gas concentration waveform. The system of the present invention is capable of performing the following basic functions: (1) identification of breath-by-breath inspired/expired end-tidal gas concentrations of three or more other expired gases (i.e., $O_2$, $NO_2$, and a volatile anesthetic); (2) calculation of the respiratory, inspiratory, and expiratory periods; (3) calculation of the respiratory rate and inspiratory/expiratory ratio; and (4) calculation of the multi-breath and time-trend averages.

An important feature of the invention system is the breath detection algorithm which is implemented in two phases—initialization and normal. The initialization phase tests for presence of a respiratory signal then determines the parameters necessary for the normal search phase. Initialization of the system requires no prior knowledge of the respiratory rate, end-tidal differences, or breathing type. The search method implemented in the normal search phase determines the occurrence of a breath by identifying the end-tidal inspired value for the next breath. Two independent search methods are used. Each method identifies a potential candidate inspiration value. The candidate inspiration values are tested for appropriate amplitude. If the candidate inspiration value fails to satisfy predetermined values, the search process continues until a valid candidate is found or the detection search is reinitiated. In a situation where two candidate inspiration values are located, an arbitration procedure is implemented to determine whether one or both of the candidate inspired values is appropriate.

Subsequent to the detection of the feature parameters using the methods described above, end-tidal values for the additional gas channels are defined to occur simultaneously with the respective expired $CO_2$ values. Inspiratory, expiratory, and respiratory periods can be calculated as the time differences between the identified feature parameters. In addition, the inspiratory/expiratory ratio can be calculated as a simple period ratio.

BRIEF DESCRIPTION OF THE DRAWINGS

FIG. 14 is a graphical representation of a typical respiratory waveform showing a summary of the results of processing the first breath using the detection algorithm of the present invention.

DETAILED DESCRIPTION OF THE PREFERRED EMBODIMENT

Figure 1:
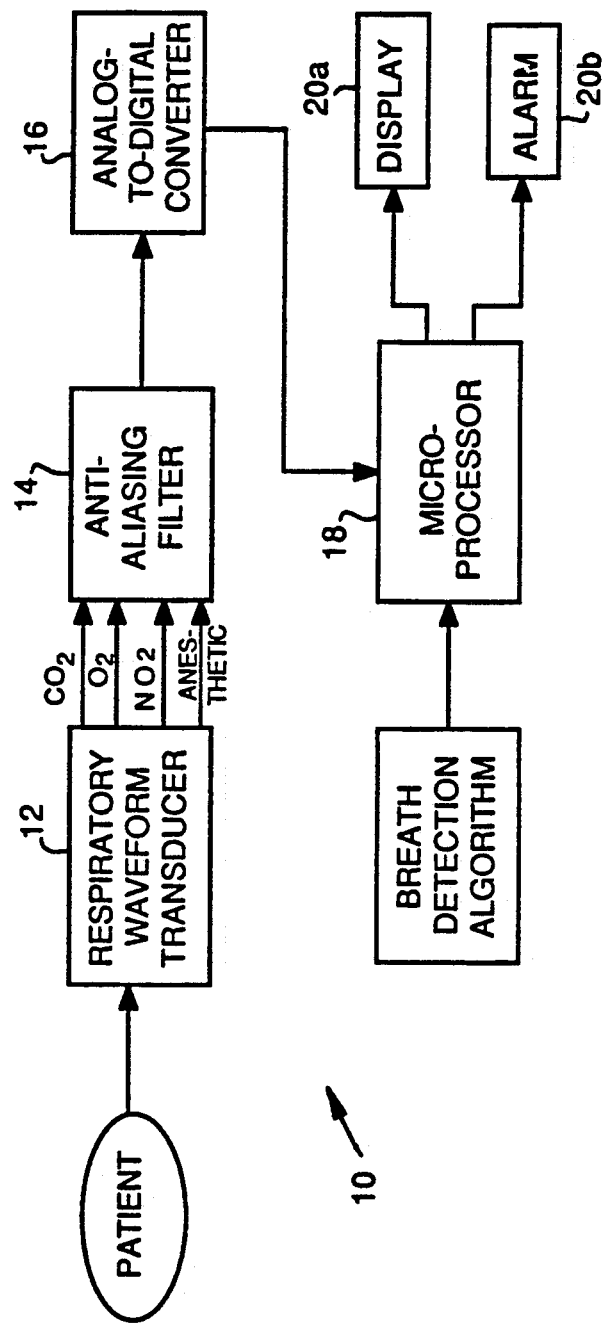
FIG. 1 is a schematic diagram of the end-tidal respiratory monitor of the present invention.

FIG. 1 is a schematic block diagram of the end-tidal respiratory monitoring system 10 of the present invention. The system is broadly comprised of a respiratory waveform transducer 12 which detects the patient's respiratory waveforms and produces an appropriate electrical output signal in response thereto. The output signal of the transducer 12 is filtered by an anti-aliasing filter 14 and is converted into digital form by an analog-to-digital converter 16. The digital output signal of the analog-to-digital converter is provided to a microprocessor 18, or other programmable processing means, which processes the respiratory signals in accordance with a breath detection algorithm, described in greater detail below.

The system can be used to implement a novel breath detection method which uses only the expired $CO_2$ gas concentration to determine end-tidal concentrations in non-$CO_2$ expired gas channels. The end-tidal monitor of the present invention is capable of operating in real time to perform the following functions: (A) identification of breath-by-breath inspired/expired end-tidal gas concentrations for $CO_2$ and other expired gases (i.e., $O_2$, $N_2O$, and an anesthetic); (B) calculation of the respiratory, inspiratory, and expiratory periods; and (C) calculation of the respiratory rate and inspiratory/expiratory ratio. In addition, the system can be adapted to use the calculated physiologic values to display or plot acute and trend data and to provide cautionary upper/lower end-tidal threshold alarms.

In the invention system, breath detection, end-tidal occurrence, and respiratory period information is obtained using the expired $CO_2$ gas concentration waveform only. Additional gas concentration channels can be sampled in time at the point of end-tidal $CO_2$ occurrence to monitor various physiologic parameters. The end-tidal monitoring system uses the $CO_2$ inspired (ISP) and expired (EXP) occurrence to determine the ISP and EXP concentrations in other gas channels. Inspiratory, expiratory and respiratory periods, respiratory rate, and I/E ratio are calculated from the start of inspiration and expiration timing differences.

Breath detection is initiated without any prior assumptions relating to respiratory rate, breathing type, or amplitude of the respiratory waveform. Normal breath detection uses two independent search methods (window and amplitude) to independently determine inspired end-tidal candidates. These candidates reside in the breath just occurring and result in a minimum ½ breath lag in detection. The window method is amplitude independent and uses a unique window filter that greatly reduces harmful effects of rapid rate changes. The amplitude method is rate independent. An arbitration procedure is used to determine the correct inspired value. The expired end-tidal (EXP) value is the absolute maximum between the current ISP and the arbitration outcome.

The breath detection algorithm of the present invention is implemented in two phases: initialization and normal. The initialization phase tests for the presence of a respiratory signal then determines the parameters necessary for the normal search method. Initialization requires no prior knowledge of respiratory rate, end-tidal differences, or breathing type.

The normal detection phase determines the occurrence of a breath by identifying the end-tidal inspired value (ISP) for the next breath. Two independent search methods are used. Each method identifies a possible ISP, which will hereafter be referred to as "candidate" ISP's. Candidate ISP's are tested for appropriate amplitudes. If a candidate inspired amplitude is not appropriate, the search method is continued until a valid candidate is found or the detection search is reinitiated. An arbitration procedure, described in greater detail below, is used to determine if one, or both, of the candidate inspired value(s) is (are) appropriate.

Respiratory Waveform Characteristics

Figure 2:
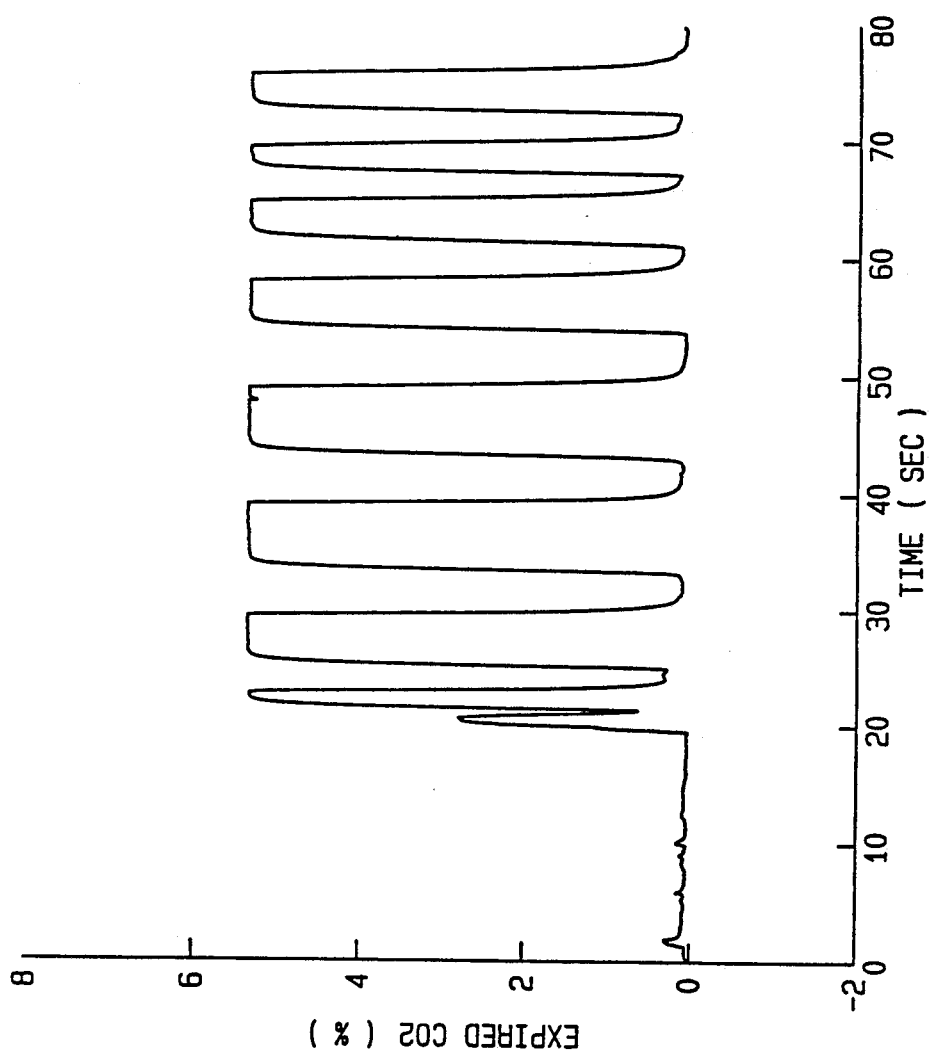
FIG. 2 is a graphical representation of a typical expired $CO_2$ time history during forced ventilation.
Figure 3:
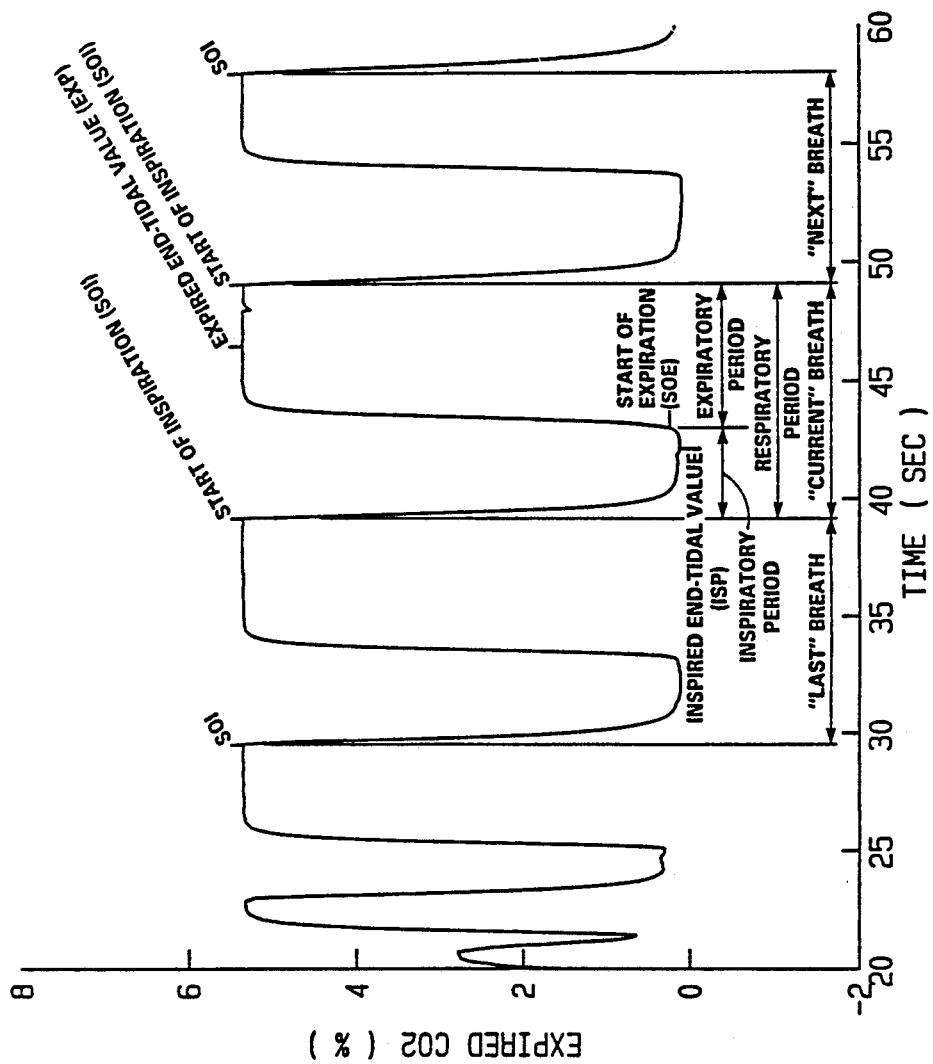
FIG. 3 is a graphical representation of the waveform of FIG. 2 showing the respiratory nomenclature used in the method of the present invention.

To understand the implementation of the end tidal detection method of the present invention, it is helpful to refer to graphical representations of respiratory waveforms contained in the accompanying figures. A typical forced ventilation expired $CO_2$ waveform is shown in FIG. 2. The small amplitude waveforms in the first 20 seconds of the record represent a typical loss of signal or ventilator start up. Breath detection is performed in an iterative manner. A three-breath reference system is used to indicate the relative position of adjacent breaths. FIG. 3 is a short time segment of forced ventilation data which is descriptively labeled with the major waveform characteristics. The breath "currently" being detected or processed is termed the "current" breath. "Next" refers to the breath that will or has already occurred after the breath currently being processed. The term "last" refers to the breath prior to the current breath.

This reference scheme is incremented after each breath determination and the subsequent breath processing or feature identification. Thus, the final step in each iteration of the breath detection/processing algorithm is to advance the reference scheme one breath. This forces the "current" breath to a "last" breath designation, the "next" breath to a "current" breath designation, and the breath occurring in the future to a "next" breath designation.

To facilitate the discussion of the method of the present invention, a short-hand notation is used for labeling key breath features. This notation will be used in all subsequent figures and discussions when referring to inspiration, expiration, start of inspiration, and start of expiration, and other respiratory values calculated using the method of the present invention. The question mark (?) symbol is used in this notation as a general purpose place holder or variable value; it represents the potential range of appropriate values. For example, a "?" in the first field would substitute for L(ast), C(urrent), or N(ext). A "?" in the last field would represent a generic value in the range 1,1,2,3 ... N.

The format used in the short-hand notation will be of the general form:

[Relative Position].[Feature Abbreviation].[Breath Number]

where the Relative Position can be indicated by variables L ("Last" breath), C ("Current" Breath), or N ("Next" Breath). The variable "?" can be equal to L(ast), C(urrent), or N(ext)

For the Feature Abbreviation notation:
ISP=end-tidal inspired value
EXP=end-tidal expired value
SOI=start of inspiration
SOE=start of expiration.

For the Breath Number:
I=result of initialization phase
1... N=result of processing breath N
?=I,1,2,3, ... N The short-hand notation outlined above can be illustrated by the following examples:

L.ISP.I="last" breath's inspired value referenced in the initialization phase

C.SOE.1="current" breath's start of inspiration as referenced during the processing of breath 1

N.SOI.3="next" breath's start of inspiration as referenced during the processing of breath 3

C.EXP.?="current" breath's expired value as referenced during processing of a generic breath It is important to note that in the notation used in the method of the present invention: N.SOI.1=C.SOI.2=L.SOI.3. Furthermore, only the C.?.? values are reported.

The start of inspiration (SOI) marks the end of the previous breath. It is characterized by a sudden $CO_2$ concentration decrease from the higher expired alveolar gas concentration to the lower fresh gas concentration. This "knee," or maximum negative acceleration in $CO_2$ concentration, represents the gas interface between expired alveolar gases and inspired fresh gases detected at the transducer interface. Conversely, the start of expiration (SOE) is the point of maximum positive acceleration in the $CO_2$ waveform and represents the shift from fresh inlet gases to expired alveolar gases.

The physical movement of gases during inspiration or expiration occur earlier than the effects observed in the expired gas waveform. In the case of inspiration, this time delay represents the period necessary to clear residual expired gases from the inlet source. Expiratory delay is the result of clearing inspired gases from the metabolically inert upper brachial tree and inlet system. For the sake of computational simplicity, the time delay between physical start of inspiration and expiration, and the resultant changes in $CO_2$ concentration, are assumed to be constant.

The sharpness or rate of $CO_2$ concentration change is a function of the inhalation and exhalation velocities. Forced ventilation is typified by rapid SOI and SOE transitions. This produces expired $CO_2$ waveforms that approach a square wave shape. The expiratory phase during spontaneous breathing is typically more rounded and represents a post-expiration relaxation phase and a less forceful inspiratory phase. Spontaneous SOE is usually similar to forced ventilation.

The inspiratory period is the time difference between the C.SOI and the C.SOE. Expiratory period is calculated as the time difference between the C.SOE and the N.SOI. Thus, the respiratory period is the sum of the inspiratory and expiratory periods or the time difference between the C.SOI and the N.SOI.

The minimum point occurring during the inspiratory phase is considered to be the inspired tidal value or ISP. Conversely, the maximum during the breath (expiratory phase) phase corresponds to the expired end-tidal value (EXP). The ISP amplitude is equal to the $CO_2$ concentration of the inlet source, and the EXP amplitude is assumed to be alveolar concentrations. End-tidal concentrations being monitored by the system in other gas channels are assumed to occur at the same instant in time as the $CO_2$ end-tidal values. Thus, end-tidal determination in additional gas channels is reduced to recording the gas concentration at the same point in time as the $CO_2$, ISP and EXP were determined.

The inspiratory/expiratory (I/E) ratio is the ratio of the inspiratory period to the expiratory period. The I/E ratio is important during forced ventilation. It indicates the relative alveolar gas retention time during a forced ventilatory breath and influences blood gas parameters. Calculated I/E ratio can also be used as a check of ventilator performance.

Breath Detection

The breath detection method of the present invention is implemented by an ordered sequence of linear searches for specific anatomic waveform conditions in the expired $CO_2$ waveform. These searches are of two types: bounded and forward-looking. The bounded search is a search that is contained between two known points. Since the two end points are known and resident in the memory of the microprocessor, all data to be searched is available to the search algorithm at the time of the bounded search.

Only the starting point for a forward-looking search is a known value. A forward-looking search starts from a known point and searches forward in time until it finds a specific waveform condition. The forward search algorithms minimize detection delays by sequentially processing all available or unsearched data currently available in the system memory. The search algorithm determines the maximum amount of data available for an intermediate search and then uses a bounded form of the search algorithm to process the intermediate data section. If the search condition is met, the value will be recorded, and the search will be ended. If no new data is available, the algorithm will stop and wait until new data has become available.

Forward searches are prevented from "running away," or running forever, by imposing a maximum search limit. If the maximum search limit is reached, the search returns an error condition.

Low Level Search Primitives

The breath detection algorithm uses three major classes of low level search techniques: (1) absolute maximum or minimum within a window; (2) confirmed maximum or minimum within a window; and (3) the next value greater or lesser than a search criteria. These lower level methods search linearly through a specified data set until a specific waveform feature or end condition has been met. Two data sets are processed using these techniques: the expired $CO_2$ gas concentration and the second difference of the $CO_2$ gas concentration. The former is used for ISP and EXP determinations. The latter is an approximation of the $CO_2$ concentration acceleration and is used in the SOI and SOE determinations.

The absolute maximum or minimum search is implemented only as a bounded search. Two independent search routines, hereafter referred to as FIND_ABS_MAX and FIND_ABS_MIN, are used to inclusively search the given data set to identify the absolute maximum or minimum, respectively. A confirmed maximum search, CONFIRMED_MAX, is a forward-looking variant of the bounded absolute maximum search. A series of bounded absolute maximum searches over a pre-determined window length are performed until the maximum returned by the FIND_ABS_MAX routine is also the first point in the window. If the maximum is not the first data point, the window is effectively moved so that it starts at the previously returned maximum. The procedure is continued until the returned maximum is the first data point in the window.

This technique has been optimized to search only the part of the new window tht has not previously been searched and to appropriately compare the results of the truncated search to the previously returned maximum. If the original maximum is greater, that maximum is confirmed within the search window. If the confirmation fails, the search window is advanced to the latest maximum; and the optimized search is continued. Similarly, a confirmed minimum (CONFIRMED_MIN) search uses FIND_ABS_MIN to identify the first confirmed minimum within the search window.

A "next greater than" (NEXT_GT) search primitive performs a bounded or forward-looking linear search for the next data value that exceeds a given search criteria. Similarly, the "next less than" (NEXT_LT) primitive returns the next data value less than the given search criteria. These two primitives are used to identify the leading and trailing edges of the expired waveform.

The above-described search primitives can be implemented using data processing techniques which are known in the art. Therefore, the specific details relating to said routines have not been included herein.

Amplitude Rejection Criteria

Candidate ISP and EXP values are tested for appropriate amplitudes before they are accepted as valid end-tidal values. The candidate end-tidal amplitude is compared to a rejection criteria to determine if the value is outside acceptable limits.

This criteria is a pre-defined ratio of the last breath's end-tidal range. The rejection criteria ratio is implemented as an integer constant multiplier and an integer constant divisor. Candidate values outside the acceptable threshold criteria are rejected, and the search is continued.

Figure 4:
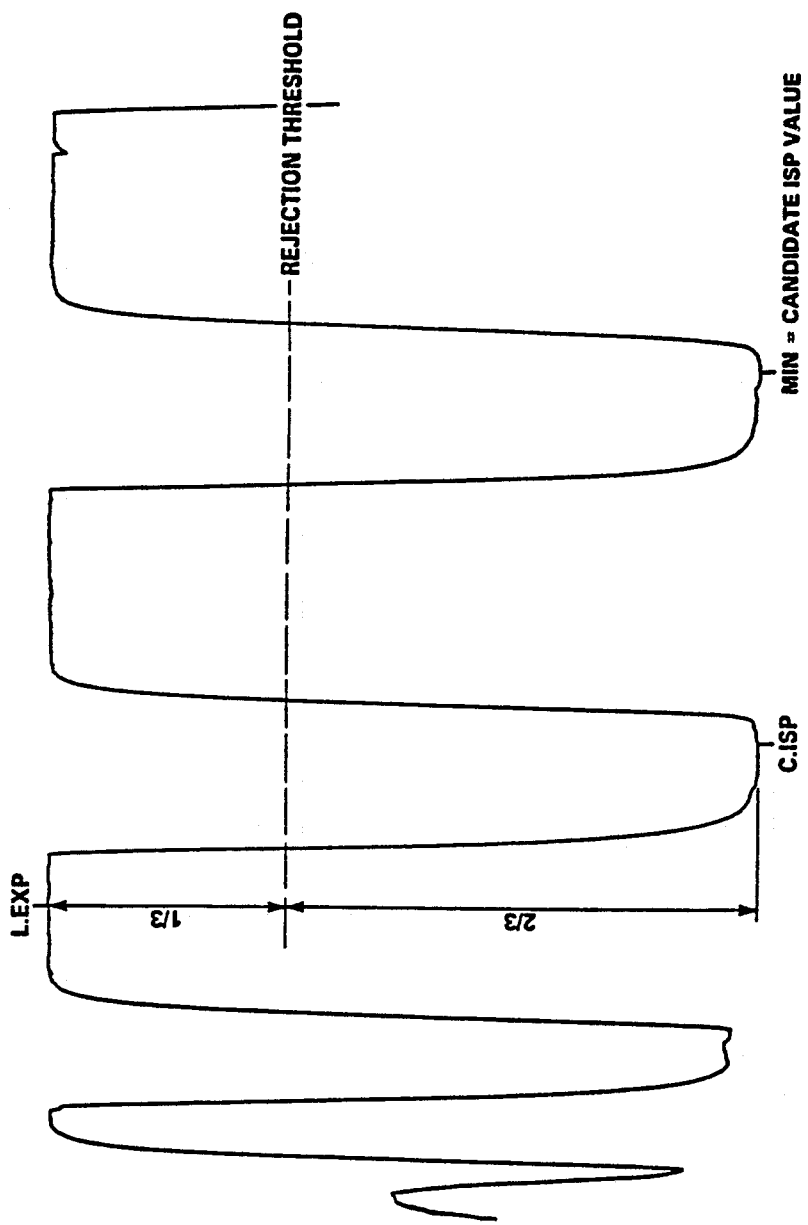
FIG. 4 is a graphical representation of a respiratory waveform illustrating the minimum amplitude rejection criteria for amplitude and window searches used in the method of the present invention.

FIG. 4 is a graphical representation of a respiratory waveform showing the rejection threshold for validating candidate ISP values. The rejection ratio is determined by integer numerator and denominator constants: MIN_REJECT_MULT and MIN_REJECT_DIV, respectively. The two constants are parameters which can be varied to change the rejection threshold. In the preferred embodiment of the invention, the constants have been selected to provide a rejection ratio which is ⅗ of the last breath's end-tidal range. Thus, the candidate ISP (MIN) is rejected if:

$$MIN > \frac{(MIN\_REJECT\_MULT)*(L.EXP-C.ISP)}{(MIN\_REJECT\_DIV)} + C.ISP \quad (EQ. 1)$$

Figure 5:
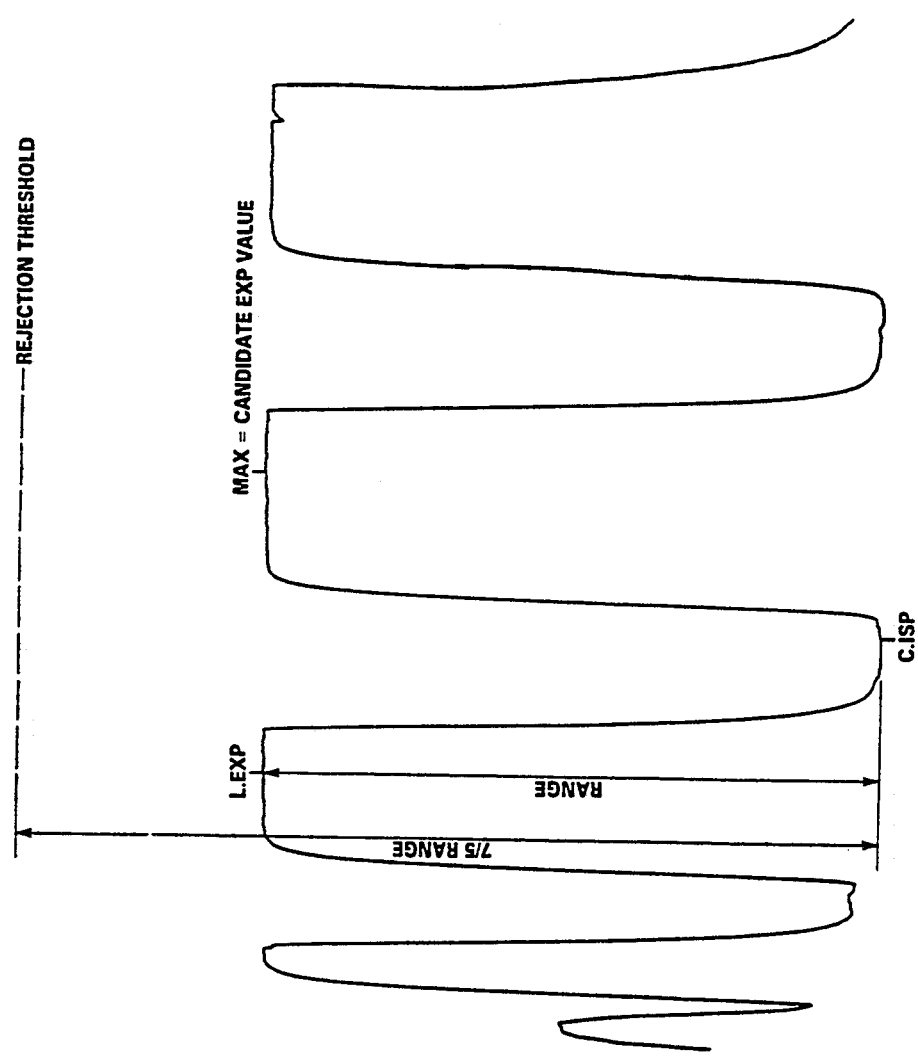
FIG. 5 is a graphical representation of a respiratory waveform illustrating the maximum amplitude rejection criteria for amplitude and window searches used in the method of the present invention.

Similarly, FIG. 5 is a graphical representation of a respiratory waveform showing the rejection threshold for validating a candidate EXP value based on the maximum rejection criteria. The rejection ratio is determined by integer numerator and denominator constants: MAX_REJECT_MULT and MAX_REJECT_DIV, respectively. The two constants are parameters which can be varied to change the rejection threshold. In the preferred embodiment of the invention, the constants have been selected to provide a rejection ratio which is 7/5 of the last breath's end-tidal range. Thus, the candidate EXP (MAX) is rejected if:

$$MAX > \frac{(MAX\_REJECT\_MULT)*(L.EXP-C.ISP)}{(MAX\_REJECT\_DIV)} + C.ISP \quad (EQ. 2)$$

SOI/SOE Determination

SOI value is defined to occur at the point of maximum negative acceleration in the expired $CO_2$ waveform. SOE occurs at the point of maximum positive acceleration. The second difference of the gas concentration is used as the estimate of the acceleration. SOI is found using an absolute minimum search bounded by ISP and EXP. Similarly, SOE is the absolute maximum after EXP and the following ISP.

Initialization Phase

Normal breath detection is not self-starting and requires L.ISP, L.EXP, C.ISP and respiratory period information to begin. However, the initialization phase (MODE_0) determines the necessary information without respiratory rate, amplitude, or breathing pattern assumptions.

Figure 6:
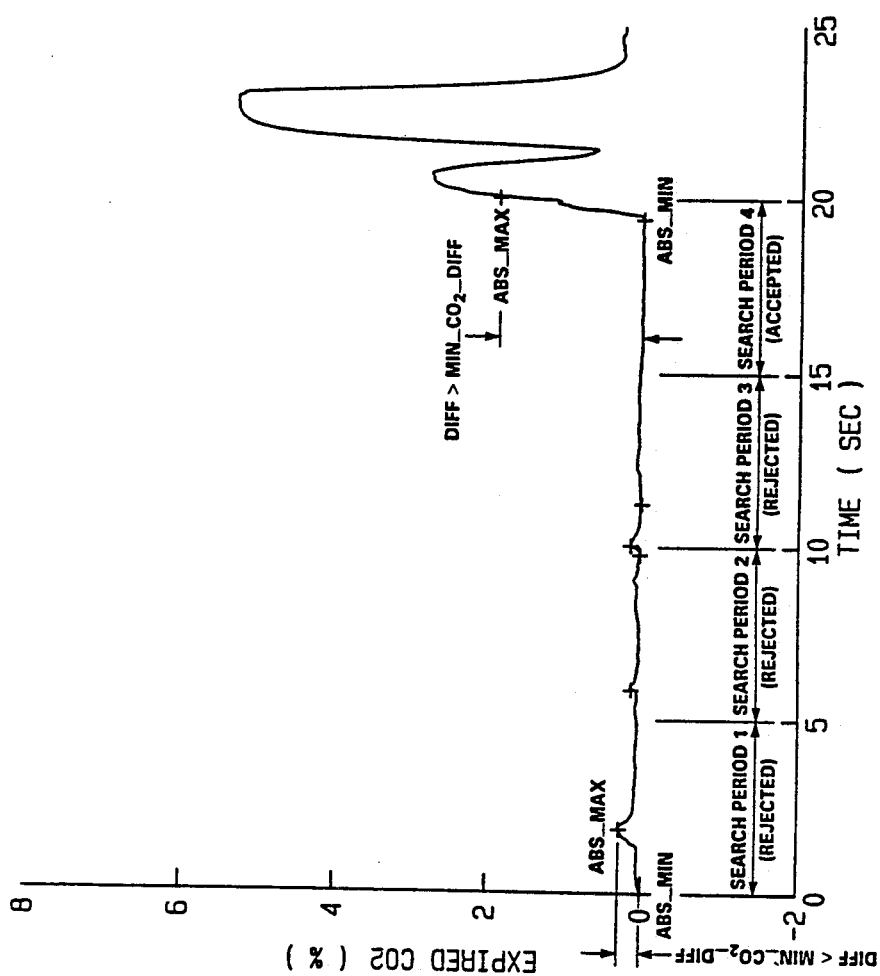
FIG. 6 is a graphical representation of a respiratory waveform illustrating the signal detection criteria for the initialization algorithm used in the method of the present invention.

The first step in MODE_0 is to determine if an adequate respiratory signal is present. A respiratory signal is present when the expired $CO_2$ concentration variation within a pre-defined search period exceeds a minimum value (MIN_CO2_DIFF). FIG. 6 is a graphical illustration of a respiratory waveform showing signal detection criteria based on the expired $CO_2$ concentration variation.

In the preferred embodiment, the MIN_CO2_DIFF is set at 0.5% $CO_2$ and the search period is defined to be 5 seconds, although each of these parameters could be varied without departing from the principles of the present invention. $CO_2$ variation is determined by calculating the amplitude difference between the absolute maximum (ABS_MAX) and the absolute minimum (ABS_MIN) within the fixed-length period. If the difference (DIFF) is less than the MIN_CO2_DIFF, the next search period is examined. Signal detection continues until MIN_CO2_DIFF is exceeded.

Figure 7:
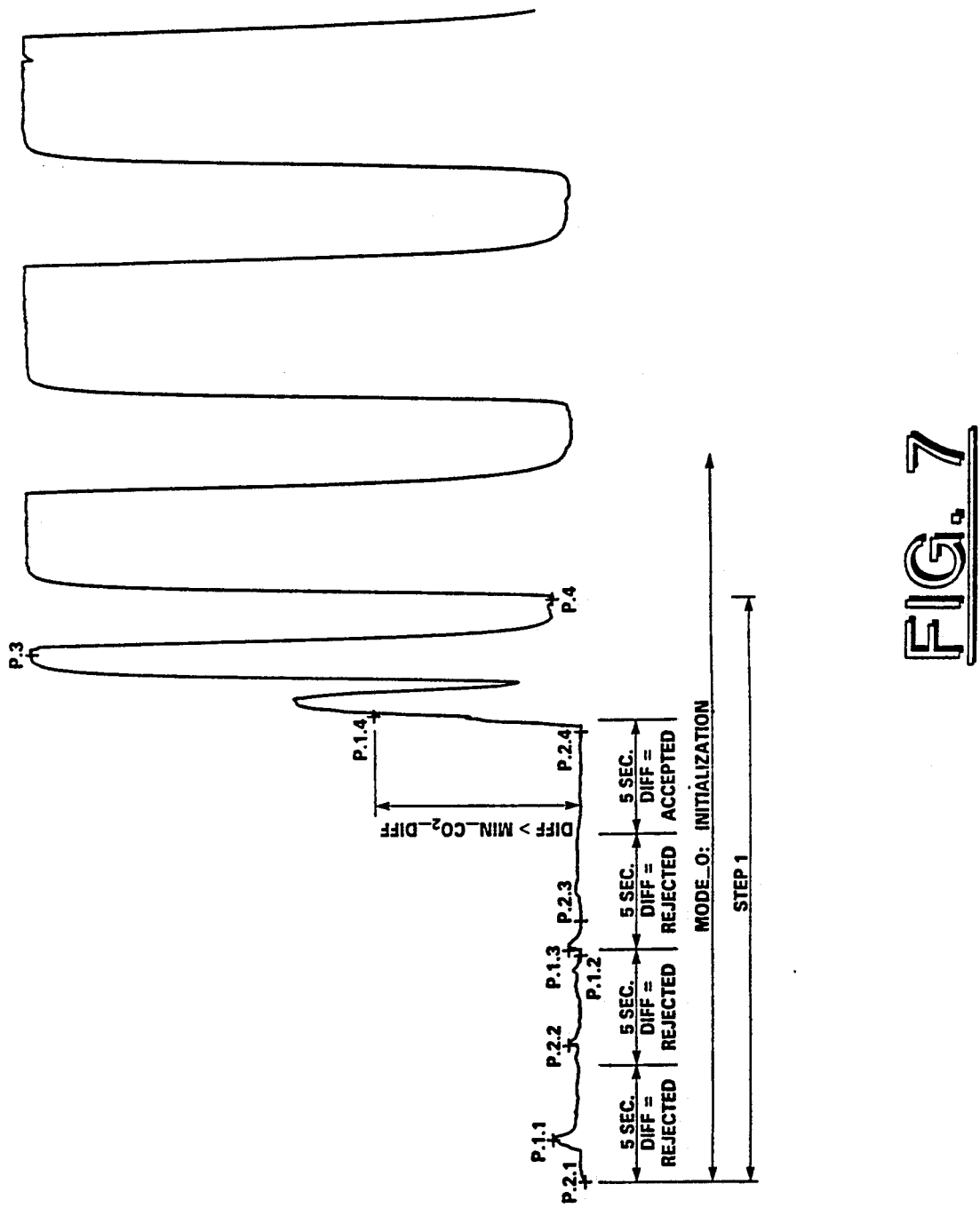
FIG. 7 is a graphical representation of a respiratory waveform illustrating the results obtained using the initialization signal detection criteria illustrated in FIG. 6.

FIG. 7 is an example of a respiratory waveform for which twenty seconds of data were searched before a 5-second search period exceeded the signal detection criteria. The notation P.1.? and P.2.? has been used to label the ABS_MAX and ABS_MIN, respectively, within the period, where the ? is the iteration count. Thus, P.1.1 and P.2.1 mark ABS_MAX and ABS_MIN for the first search period. In this example, a forward-looking FIND_ABS_MAX search was used to find P.1.? and a bounded FIND_ABS_MIN to determine P.2.?. P.3 is the result of a forward search confirmed maximum search within a search time constant (TC) window and should be the maximum of the breath following P.1.4. TC is initialized to 2.5 seconds. A forward looking confirmed minimum with a TC window is used to estimate a candidate L.ISP.I (P.4).

Figure 8:
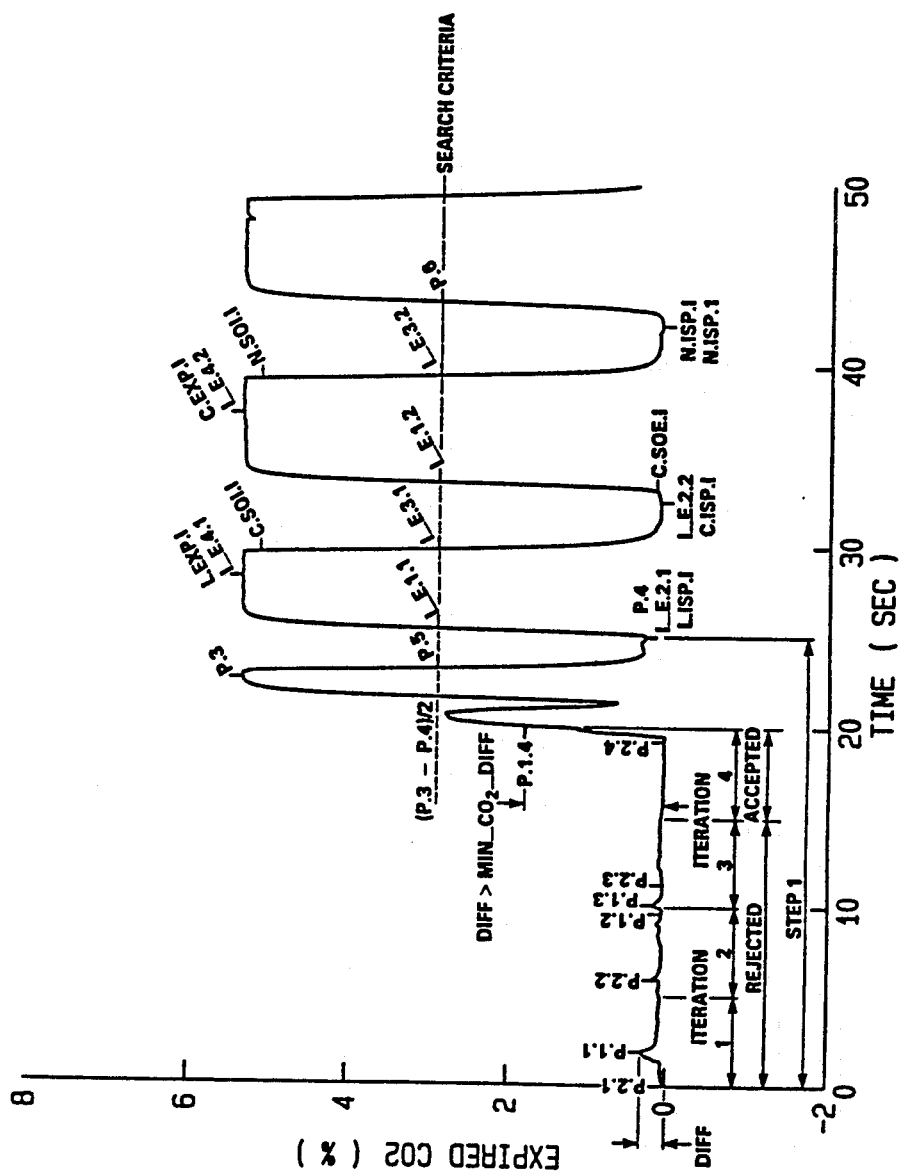
FIG. 8 is a graphical illustration of a typical respiratory waveform summarizing the results of the initialization algorithm of the present invention.

Subsequent to the identification of the above-described features, a series of next greater and less than searches are used to identify leading and trailing edges. These features are identified on the respiratory waveform shown in FIG. 8. The search criteria for these searches is the mid-range point between the best estimate of end-tidal minimum and maximum, (P.3-P.4)/2. The leading edge occurs between SOE and EXP, and the trailing edge occurs between SOI and ISP. Candidate ISP's are the absolute minimums between trailing and leading edges, while candidate EXP's are the absolute maximum between leading and trailing edges. Candidate ISP's and EXP's are tested using the MIN_REJECT and MAX_REJECT criteria. The following is a summary of the features identified in FIG. 8. Wherever possible, the shorthand notation using generic place holders has been used for the defined features:

P.1.? = Absolute maximum in search window
P.2.? = Absolute minimum in search window
P.3 = Confirmed maximum in a TC window (2.5 sec)
P.4 = Confirmed minimum in a TC window (2.5 sec)
P.5 = Next value less than search criteria after P.3 (trailing edge determination)
L_E.1.? = Next value greater than search criteria after previous trailing edge determination (leading edge)
L_E.2.? = Absolute minimum between trailing and leading edge
?.ISP.I = L_E.2.?
L_E.3.? = Next value less than search criteria after L_E.1.? (Trailing edge)
L_E.4.? = Absolute maximum between L_E.1.? and L_E.3.?
?.EXP.I = L_E.4.?
P.6 = Next value greater than search criteria after L_E.3.2
N.ISP.I = Absolute minimum between L_E.3.2. and P.6

Figure 9:
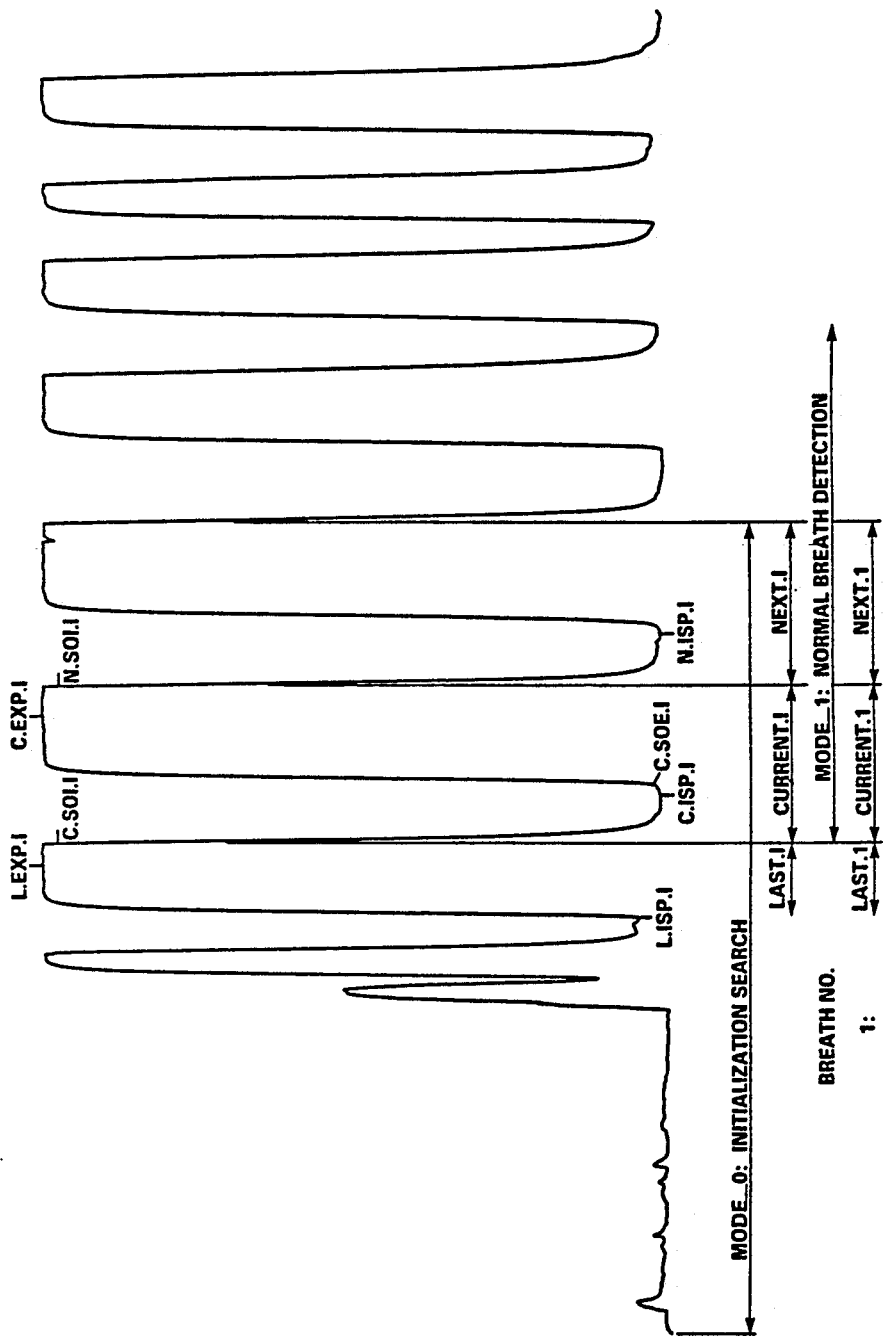
FIG. 9 is a graphical representation of a respiratory waveform illustrating the search results for the first application of normal breath detection using the method of the present invention.

FIG. 9 is a graphical representation of a respiratory waveform summarizing the major respiratory features determined during the MODE_O phase. Subsequent to the MODE_0 search, the normal breath detection algorithm (MODE_1), is used to iteratively process all subsequent breaths. In the preferred embodiment, MODE_0 does not increment the relative breath referencing system. Thus the initial processing step in MODE_1 results in reprocessing of the same breath as MODE_0.

Normal Breath Detection Search

Normal breath detection is initiated by using two independent forward-looking search methods to correctly identify the N.ISP. These independent techniques are the window and the amplitude search technique. Both the window and the amplitude search techniques use forward-looking searches to identify the candidate N.ISP values. Breath detection occurs in real-time with a minimum of ½ breath lag due to the need to define the leading edge after the N.ISP.

Amplitude Search Technique

Figure 10:
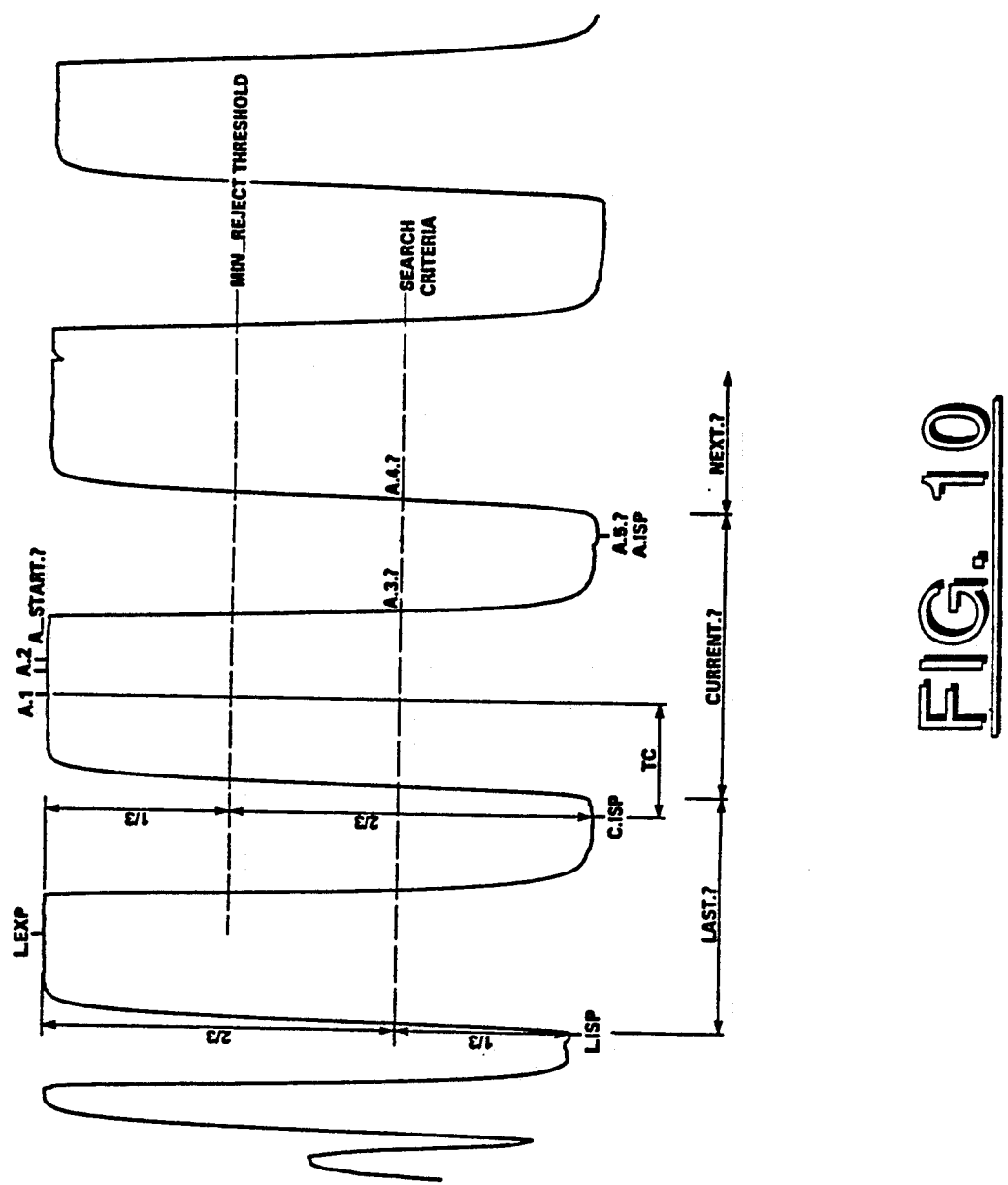
FIG. 10 is a graphical illustration of a typical respiratory waveform illustrating the amplitude search method of the present invention.

The amplitude search technique, FIG. 10, is based on sequentially searching for the next occurrence of a predetermined gas concentration in order to identify the minimum between the trailing edge (A.3.?) and the leading edge (A.4.?). In the preferred embodiment of the present invention, the search criteria is ⅓ of the expiratory range. For the feature parameters illustrated in FIG. 10, A.1 represents an absolute maximum within a TC window and A.2 represents the next value greater than the search criteria after A.1. The point A_START is the starting point for trailing edge determination and it is initialized to A.2+1. A.3.? is the trailing edge after A_START and A.4.? is the leading edge after A.3.?. A.5.? is the candidate absolute minimum between A.3.? and A.4.?. The candidate minimum value (A.5.?) must be below the MIN_REJECT criteria to be returned as the candidate amplitude ISP (A.ISP). In the preferred embodiment of the invention system, the MIN_REJECT criteria is set at ⅔(L.EXP−L.ISP)+L.ISP. If the MIN_REJECT test fails, the iterative A.5.? search will be continued at (A_START+TC).

This search technique is amplitude dependent and frequency independent. The search criteria ratio of ⅓ is conservative for breath-by-breath changes in EXP but sensitive to sudden increases in ISP. However, the present invention is not intended to be limited to this specific ratio. For example, a ratio of ½ could be used while maintaining adequate sensitivity to changes in both ISP and EXP.

Window Search Technique

Figure 11:
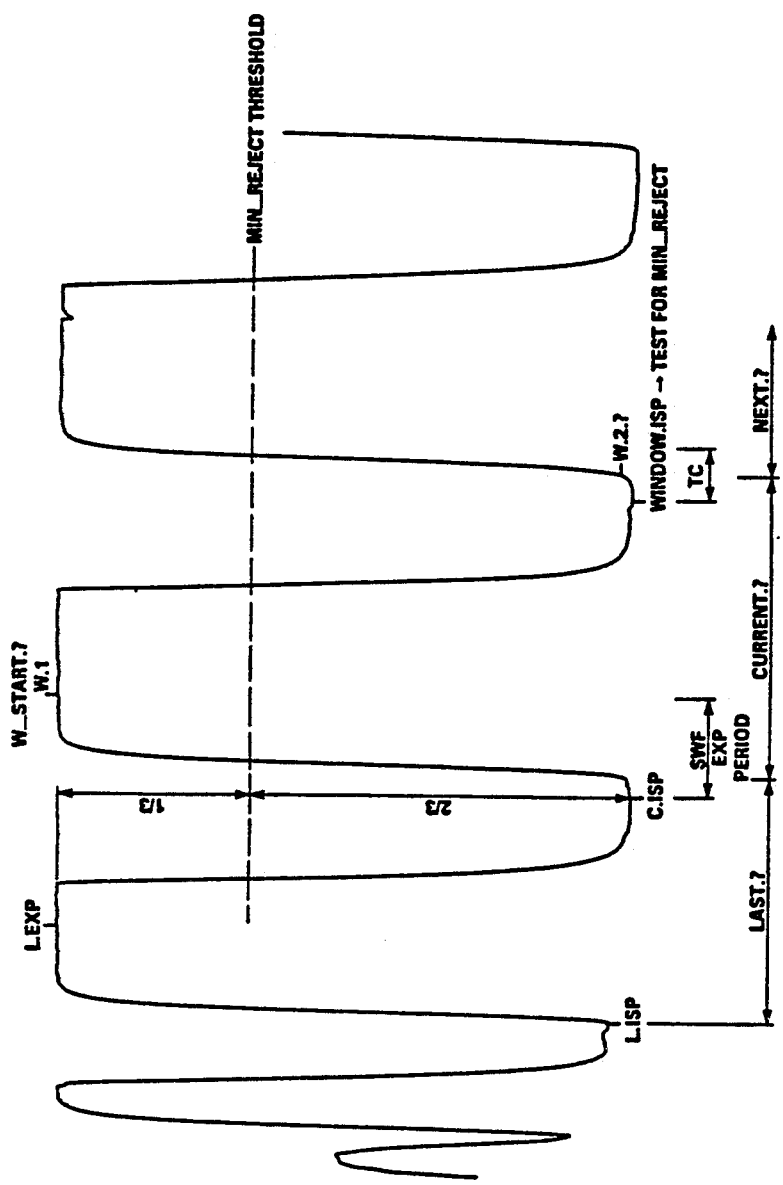
FIG. 11 is a graphical illustration of a typical respiratory waveform illustrating the window search method of the present invention.

Conversely, the window search method, illustrated in FIG. 11, uses a sequence of confirmed minimum searches to determine the N.ISP. Since it is a window-based search, it is frequency dependent and amplitude independent. It has been determined experimentally that overly large window widths cause the search method to skip or miss faster, shorter breaths. To reduce the effects of rapid changes in respiratory rate, the confirmed search window width is an adaptive function of the prior expired period history. In the preferred embodiment, a filtering technique is used to weight a multi-breath expired period history towards the smaller periods contained within it. This filter is tunable and has been termed the smallest weighted filter (SWF). The SWF of the preferred embodiment is insensitive to the two largest expired periods out of the last 5 breaths and is sensitive to the smallest 3 out of 5. The SWF is implemented by a histogram sorting technique which produces an output equal to the weighted average of the 3 smallest values in an array 5 total values. The SWF expired period is multiplied by 0.6 to reduce the window's sensitivity further. Use of the SWF has greatly enhanced the tolerance of the window search method to rapidly changing respiratory rates. For the feature points illustrated in FIG. 11, TC is defined to be 0.6*(SWF output of the last 5 expired periods). In the preferred embodiment, the MIN_REJECT criteria for this search is defined as ⅔ *(L.EXP−L.ISP)+L.ISP and the SWF EXP period is defined as TC/0.6. W.1 is the absolute maximum within the window defined by (1/0.6)*(TC). W_START is the starting point for the confirmed minimum search and W.2.? is the minimum confirmed value within the TC window after W.1, or (W.2.?−1+TC). W.ISP is the first W.2.? which was less than the MIN_REJECT threshold and is equal to the candidate N.ISP from the window search technique.

Both search methods will return only one N.ISP candidate, with each of the potential candidates having an acceptable amplitude. An arbitration procedure, described below, is then used to identify the best N.ISP value from those identified in each of the searches.

Amplitude/Window Candidate Arbitration

Figure 12A:
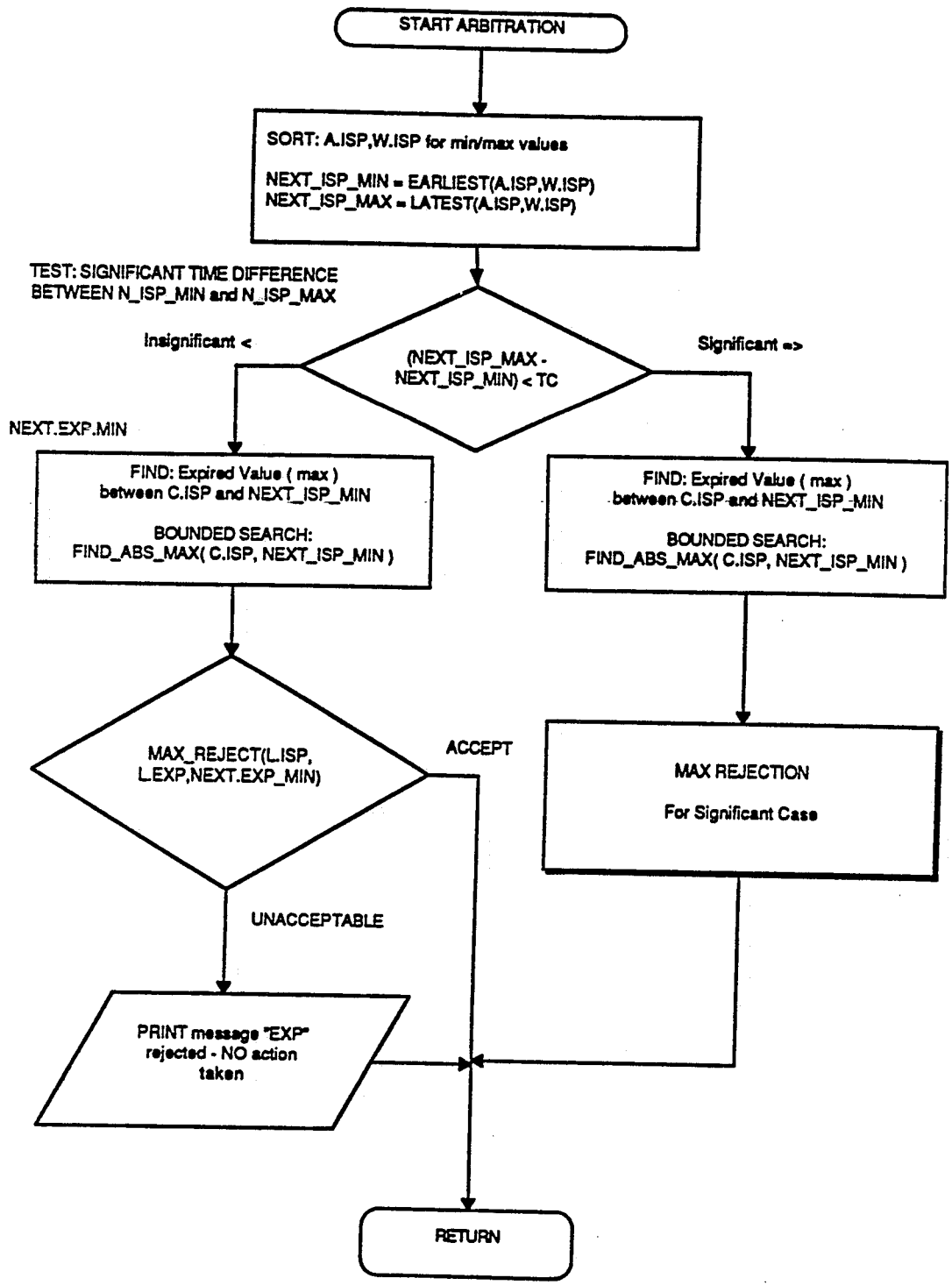
FIGS. 12a and 12b are flow chart summaries of the arbitration method used in the end-tidal detection method of the present invention.
Figure 12B:
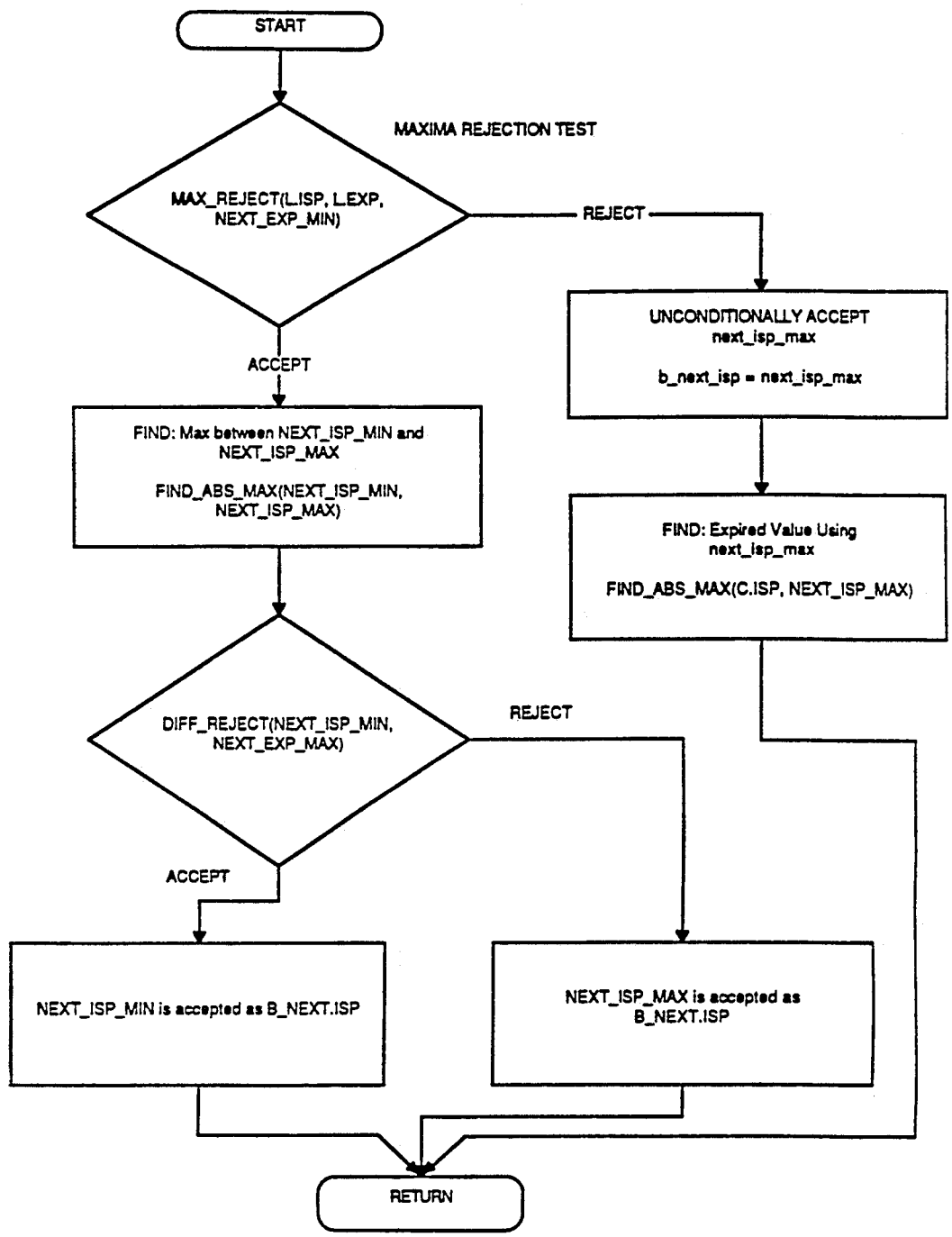
Figure 13:
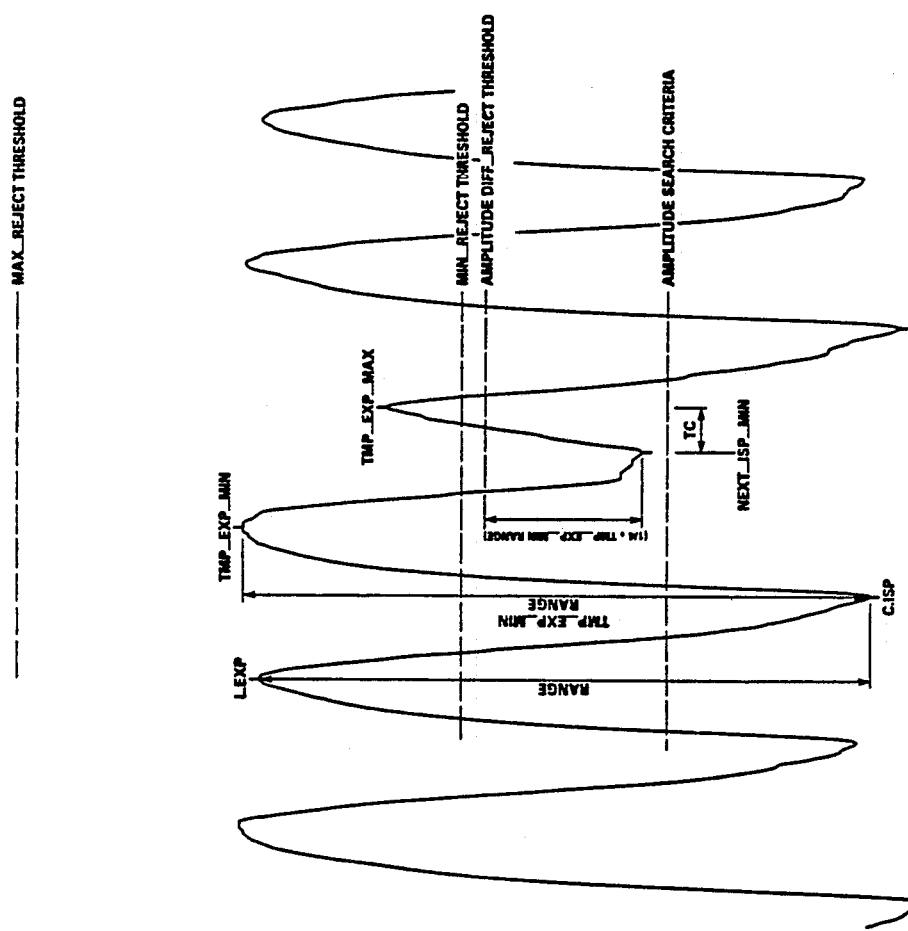
FIG. 13 is a graphical illustration of a typical respiratory waveform showing a summary of the normal search arbitration and rejection criteria of the detection method of the present invention.

For the case where two acceptable candidate ISP values have been identified by the above-described techniques, an arbitration process is used to determine which of the two search outcomes correctly defines the end of the present breath. This arbitration is based on: (1) time differences between the two outcomes, and (2) the appropriateness of ESP values for each breath as defined by the window and the amplitude methods. The flow chart in FIGS. 12a and 12b shows the computational steps used in the arbitration process. FIG. 13 is a graphical representation of a respiratory waveform illustrating all rejection and arbitration criteria discussed above.

Subsequent to the identification of the feature parameters using the methods described above, end-tidal values for the additional gas channels are defined to occur simultaneously with the respective expired $CO_2$ values. Other low frequency data sources (i.e., oximeter saturation) could be sampled, determined, and displayed on a breath-by-breath basis. Inspiratory, expiratory, and respiratory periods can be calculated as the time differences (C.SOE−C.SOI), (N.SOI−C.EXP), and (N.SOI−C.SOI), respectively. The inspiratory/expiratory (I/E) ratio is calculated as a simple period ratio. FIG. 14 is a graphical illustration of a respiratory waveform summarizing the features identified in the first iteration of MODE_1.

While the method and apparatus of the present invention has been described in connection with the preferred embodiment, it is not intended to limit the invention to the specific form set forth herein, but on the contrary, it is intended to cover such alternatives, modifications and equivalents as may be included within the spirit and scope of the invention as defined by the appended claims.

We claim:

1. An end-tidal respiratory monitor, comprising:
means for detecting a respiratory waveform comprising only expired carbon dioxide produced by a patient during a predetermined time interval and producing an electrical signal representation thereof;
programmable analyzer means adapted to receive said electrical signal representation of said respiratory waveform, said analyzer means further comprising means for calculating the inspiratory, expiratory and respiratory periods of said respiratory waveform of said patient and for producing respective output signals for each said period; and
display means for indicating the respiratory characteristics of said patient corresponding to said respective output signals of said analyzer means.

2. The monitoring system according to claim 1, said means for calculating said respective periods comprising an amplitude search algorithm which is independent of the frequency of said respiratory waveform.

3. The monitoring system according to claim 2, said means for calculating said respective waveforms further comprising a window search algorithm which is independent of the amplitude of said respiratory waveform.

4. The monitoring system according to claim 3, said means for analyzing said respective waveforms further comprising means for arbitrating between the output produced by said amplitude search algorithm and said window search algorithm.

5. The monitoring system according to claim 4, said window search algorithm further comprising a weighted filter, said filter being insensitive to rapid changes in said respiratory waveform.

6. An end-tidal respiratory monitor comprising:
means for detecting a respiratory waveform comprising only expired carbon dioxide produced by a patient during a predetermined time interval and producing an electrical signal representation thereof;
programmable analyzer means adapted to receive said electrical signal representation of said respiratory waveform, said analyzer means further comprising first and second algorithms for calculating the inspiratory, expiratory and respiratory periods of said respiratory waveform of said patient and for producing respective output signals for each said period, said first algorithm being independent of the frequency of said respiratory waveform, said second algorithm being independent of the amplitude of said waveform; and
display means for indicating the respiratory characteristics of said patient corresponding to said respective output signals of said analyzer means.

7. The monitoring system according to claim 6, said means for analyzing said respective waveforms further comprising means for arbitrating between the outputs produced by said first algorithm and said second algorithm.

8. The monitoring system according to claim 8, said second algorithm further comprising a weighted filter, said filter being insensitive to rapid changes in said electrical signal representation of said respiratory waveform.

* * * * *